United States Patent
Braun et al.

(12)

(10) Patent No.: US 6,252,105 B1
(45) Date of Patent: Jun. 26, 2001

(54) SYNTHESIS OF LOW-FLUORIDE ORGANIC COMPOUNDS

(75) Inventors: Max Braun, Wedemark; Johannes Eicher, Oedheim, both of (DE); Francine Janssens, Vilvoorde (BE); Kerstin Eichholz, Langenhagen (DE); Stefan Palsherm, Barsinghausen (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 0 days.

(21) Appl. No.: 09/348,072

(22) Filed: Jul. 6, 1999

Related U.S. Application Data

(60) Provisional application No. 60/096,163, filed on Aug. 11, 1998.

(30) Foreign Application Priority Data

| Jul. 6, 1998 | (DE) | 198 29 909 |
| Oct. 30, 1998 | (DE) | 198 50 010 |

(51) Int. Cl.⁷ .................................................. C07C 69/63
(52) U.S. Cl. .................... 560/227; 562/577; 562/578; 562/849
(58) Field of Search ........................ 562/577, 578, 562/227, 849; 560/227

(56) References Cited

U.S. PATENT DOCUMENTS

| 4,927,962 | * | 5/1990 | Aramaki et al. | 562/113 |
| 5,006,563 | | 4/1991 | Hamer et al. | |
| 5,405,991 | * | 4/1995 | Feist et al. | 560/239 |

FOREIGN PATENT DOCUMENTS

| 1 158 490 | 12/1960 | (DE) . |
| 20 44 986 | 3/1971 | (DE) . |
| 33 11 751 | 10/1984 | (DE) . |
| 40 23 106 | 7/1990 | (DE) . |
| 197 32 031 | 7/1997 | (DE) . |
| 0 566 974 | 10/1993 | (EP) . |
| 0 623 582 | 11/1994 | (EP) . |
| 931689 | 12/1961 | (GB) . |
| 90 11270 | 10/1990 | (WO) . |

OTHER PUBLICATIONS

Begue, J., Bonnet–Delpon, D., Mesureur, D., Nee, G., and Wu, S. (1992) "The Witteg Reaction of Perfluoro Acid Derivatives: Access to Flourinated Enol Ethers, Enamines, and ketones". *J. Org. Chem.* 57:3807–3814.

Kitazume, T., Asai, M., Tsukamoto, T., and Yamazaki, T. (1992) "A microbially–based approach for the synthesis of chiral secondary alcohols bearing the diflouromethyl or chlorodifluoromethyl group". *Journal of Flourine Chemistry* 56:271–284.

Scharbach, "Auswirkung von flusssaeureverunreinigtem Eintrag auf Chemieapparate–Email" Pflauder–Handbuch, Schwetzingen (1978).

Database Registry (Online) XP–002127114, 1999.

* cited by examiner

Primary Examiner—Johann Richter
Assistant Examiner—Brian J. Davis
(74) *Attorney, Agent, or Firm*—Crowell & Moring, L.L.P.

(57) ABSTRACT

Organic compounds, e.g. fluorinated organic compounds such as fluorinated carboxylic acids or fluorinated carboxylic acid chlorides, may contain small amounts of carboxylic acid fluorides, hydrogen fluoride or hydrolyzable fluoride, which during the preparation of derivatives of the fluorinated organic compounds, for example by esterification, may yield corrosive fluorides or hydrogen fluoride. The invention is a method for the synthesis and/or purification of preferably fluorinated organic compounds such as carboxylic acids, carboxylic acid chlorides and derivatives such as esters thereof, starting from corresponding carboxylic acid chlorides containing acid fluorides or hydrolyzable fluoride, and alcohols under the catalytic action of "onium" salts of carboxylic acids, to obtain products which have a low fluoride content. Alternatively, an inorganic oxide adsorbent is utilized. The method is especially suitable for the synthesis of esters of trifluoroacetic acid, chlorodifluoroacetic acid, trifluoroacetoacetic acid and/or difluoroacetoacetic acid.

20 Claims, No Drawings

SYNTHESIS OF LOW-FLUORIDE ORGANIC COMPOUNDS

This application claims the benefit of prior filed provisional application No. 60/096,163, filed Aug. 11, 1998 now abandoned.

BACKGROUND OF THE INVENTION

This invention relates to a method for the catalytic synthesis of low-fluoride organic compounds, especially fluorinated organic compounds such as carboxylic acids and derivatives thereof.

Fluorinated organic compounds are of great importance in many areas of technology. Fluorinated organic compounds (fluorinated hydrocarbons, fluorochlorohydrocarbons, fluorine-containing ethers, fluorine-containing surfactants, etc.) are used, for example, in the field of refrigeration technology, in the fire extinguisher field, and as cleaning agents. Fluorinated hydrocarbons are utilized as propellants for the production of foams or aerosols (even in the field of pharmaceutical preparations). Fluorinated organic compounds are used not only as end products as explained above, but also as intermediate products in the production of useful processed goods. Particularly in the field of agricultural technology, for example, fluorine- containing, and in some cases chlorine-containing, carboxylic acids have proved very interesting as building blocks. Carboxylic acids of this type and reactive derivatives thereof, such as carboxylic acid chlorides, can be further processed—frequently in condensation reactions—to yield interesting building blocks, for example esters or ring systems.

Many carboxylic acids and esters of carboxylic acids are used in industry as such. Acetate esters and other carboxylate esters are used, for example, as solvents or cleaning agents, while other esters, such as those of succinic acid, are used for aromatizing. Ethyl trifluoroacetate is, for example, a solvent for the chlorination of paraffins or for the polymerization of olefin oxides. Many carboxylate esters are also intermediates in chemical synthesis. The hydrogenation of methyl trifluoroacetate and of 1,1,1-trifluoroethyl trifluoroacetate results in trifluoroethanol (and possibly methanol). Trifluoroethanol is used as a solvent and as intermediate, for example, for the production of the solvent and anesthetic, isofluorane. Esters of trifluoroacetic acid and trifluoroacetoacetic acid are also used for the introduction or synthesis of biologically active compounds, which have a $CF_3$ group. For example, by N-acylation with methyl trifluoroacetate, peptides with hormonal activity can be synthesized. Shift reagents for NMR analysis are obtained from trifluoroethyl esters, together with camphor derivatives. After the Fries displacement with aluminum chloride, phenyl trifluoroacetate yields the corresponding trifluoroacetylated phenol, which is a building block for the synthesis of pharmaceutical drugs. Persons skilled in the art are familiar with many other applications involving esters, for example, the reactions of esters with amines to form amides, which represent building blocks for the synthesis of pharmaceutical drugs, photosensitizers and dyes.

Esters of chlorodifluoroacetic acid also are building blocks for syntheses. The ethyl ester is used, for example, for the synthesis of liquid crystals (see German Offenlegungsschrift 4 023 106) and for the synthesis of drugs (see U.S. Pat. No. 5,006,563), and the methyl ester is also used for the synthesis of liquid crystals and as a starting material for the microbial synthesis of chiral secondary alcohols (see T. Kitasume et al., J. Fluorine Chem. 56 (1992), pages 271 to 284) or for the synthesis of fluorinated enol ethers by the Wittig method (see J. P. Begue et al., J. Org. Chem. 57 (1992), page 3807 ff). The esters of chlorodifluoroacetic acid are also intermediates in the synthesis of dichlorocarbene.

Carboxylic acid chlorides, particularly fluorine-containing carboxylic acid chlorides, are reacted with ketene to form compounds of the type $RC(O)CH_2C(O)Cl$, which are esterified and also are synthesis building blocks. The synthesis of acid chlorides of halogenated acetoacetic acid and their esterification is disclosed in the German Auslegeschrift 1 158 490. The esters are intermediates in dye chemistry, pharmaceutical chemistry and crop protection chemistry.

Fluorinated organic compounds can be produced, for example, by means of direct fluorination with $F_2$, higher valence metal fluorides, through chlorine-fluorine exchange, HF-addition, and other processes. Insofar as hydrolyzable fluoride is obtained, whether as a result of the process used or through hydrolysis of fluorine from the molecule, this can lead to corrosion problems with glass, ceramic and metal containers or apparatus.

Hydrogen fluoride reacts with glass and ceramics and ultimately forms $H_2SiF_6$, which for its part under certain conditions reacts with water to form HF and $SiO_2$ again. The HF which is released again attacks glass, so that great damage can result. Corrosion of metal containers is likewise undesired.

Problems not only arise in storage/supply containers, but also in preparation of derivatives of fluorinated organic compounds, for example through condensation reactions in which HF is released, sometimes as a secondary reaction product.

However, the esterification of carboxylic acid chlorides without catalysts with alcohols leads to corrosion problems if the acid chlorides, due to the way in which they are produced, contain small amounts of carboxylic acid fluorides, free hydrogen fluoride or hydrolyzable fluoride. Such contaminants also frequently interfere in carboxylic acids or their esters because of corrosion problems.

The foregoing explanations detail the problems with fluorinated organic compounds. Such problems can also arise in compounds which are not substituted by fluorine, but which may take up fluorine as an impurity during their production.

It is surprising how often undesired corrosion can be traced back to hydrolyzable fluorides.

SUMMARY OF THE INVENTION

It is an object of the present invention to provide a method, which can be carried out easily industrially and with which organic compounds, especially fluorinated organic compounds, can be produced or purified so that they contain decreased amounts of hydrolyzable fluoride.

It is a specific object of the invention to provide a method with which carboxylic acids, carboxylic acid chlorides and derivatives thereof, especially those produced in condensation reactions, which contain little fluoride or decreased amounts of carboxylic acid fluorides and free hydrogen fluoride, can be synthesized in good yield starting from corresponding contaminated carboxylic acids, carboxylic acid chlorides or esters.

These and other objects are achieved in accordance with the present invention by providing a method for producing an organic compound with a decreased content of hydrolyzable fluoride, said method comprising the step of contacting an organic compound contaminated with hydrolyzable fluoride with at least one separating agent for hydrolyzable fluoride selected from the group consisting of inorganic oxide sorption agents and "onium" salts of carboxylic acids.

The process of the invention is suitable for purifying organic compounds which are contaminated with fluoride or hydrolyzable fluorine. This contamination may result from the production of the compound and or it may result from hydrolysis of fluorine in the molecule. Preferably fluorinated organic compounds are purified. These are compounds which contain at least one fluorine atom. Optionally, other halogen substituents can also be contained therein. The invention will be explained in further detail with reference to such embodiments.

The invention comprises two aspects: the purification of previously synthesized fluorinated organic compounds (e.g. before their use or further processing or during storage), and the synthesis of fluorinated organic compounds with simultaneous purification in accordance with the invention.

Preferably the invention is used for the synthesis or purification of fluorine-containing carboxylic acids, fluorine-containing carboxylic acid chlorides and/or for the synthesis or purification of derivatives of fluorine-containing carboxylic acids and fluorine-containing carboxylic acid chlorides. The formation of derivatives usually refers to condensation reactions such as esterification of fluorine-containing carboxylic acids or carboxylic acid chlorides, condensation with hydrazine derivatives, hydrolysis, etc.

The method of the invention can be used to good advantage with organic compounds containing one or more $CF_3$—, $CF_2H$— or $CF_2Cl$— groups.

The term "hydrolyzable fluoride" is to be understood to also include alkali fluoride, as may be generated, for example, in alkali (alkaline lye) catalyzed reactions.

The method of the invention serves preferably for the synthesis or purification of carboxylic acids, carboxylic acid chlorides and carboxylic acid esters, which are low in carboxylic acid fluoride, free HF or hydrolyzable fluorine, from carboxylic acids, carboxylic acid chlorides and carboxylic acid esters which are contaminated with carboxylic acid fluoride, HF and/or hydrolyzable fluoride, by contacting the same with at least one separating agent for carboxylic acid fluoride, free HF or hydrolyzable fluoride selected from the group consisting of inorganic oxide sorption agents (absorbents) and "onium" salts of corresponding carboxylic acids.

A preferred inorganic oxide absorbent is silicon dioxide, particularly in the form of amorphous silicon dioxide, for example, precipitated as the hydrate, or in the form of silica gel beads. A previously mentioned, water is often released in condensation reactions. This leads to the formation of HF, which in turn leads to corrosion. In the purification of substances or reaction mixtures which do not contain any further amount of water other than this water of condensation, finely divided $SiO_2$, optionally in the form of a hydrate, can be used very well as an HF scavenger. In systems which contain a larger amount of water, silica gel beads (or another coarse particulate material) are advantageously used. The beads, granules or pressed bodies can be used directly in the reactor. Preferably the material or the reaction mixture to be purified is conducted in a circuit through a separately arranged bed of particulate sorbent material. It has been found that HF-related corrosion (e.g., the formation of hexafluoro silicic acid or its renewed decomposition) is effectively suppressed, even is systems with large water contents.

When an "onium" salt is used, this HF scavenger is renewed, as soon as the molar ratio of HF to "onium" salt exceeds the value of 2:1.

The inventive method is suitable particularly for the synthesis (purification) of carboxylic acids having the formula $R^1C(O)OH$ (I), of carboxylic acids chlorides having the formula $R^1C(O)CH_2C(O)Cl$ (II), of esters having the formula $R^1C(O)OR^2$ (III) and of esters having the formula $R^1C(O)CH_2C(O)OR^2$ (IV). $R^1$ and $R^2$ are defined further below. Optionally, the purification can be carried out by using an oxide absorbent and an "onium" salt simultaneously or successively in any sequence.

After it is synthesized and optionally isolated, the ester can be purified by the inventive method. According to one embodiment of the invention, the carboxylic acid fluorides, hydrogen fluoride and hydrolyzable fluoride are removed during the synthesis of the ester from carboxylic acid chloride and alcohol.

This specific embodiment of synthesizing low-fluoride carboxylate esters from alcohols and carboxylic acid chlorides contaminated with carboxylic acid fluoride or hydrogen fluoride and hydrolyzable fluoride is characterized in that the reaction is carried under anhydrous conditions in the presence of an "onium" salt of the carboxylic acid, corresponding to the carboxylic acid chloride used, as separating agent and/or in the presence of the inorganic oxide absorbent. The carboxylate ester formed can be separated, for example by distillation. The fluoride remains behind in the residue.

Moreover, the "onium" salt of the carboxylic acid can, at the same time, function as catalyst. One possibility consists of reacting the acid chloride and the alcohol in the presence of the "onium" salt and cycling the reaction mixture over the absorbent. Of course, it is also possible to work without a catalyst or with other catalysts and to cycle the reaction mixture over an absorbent such as $SiO_2$.

The "onium" salt may optionally be synthesized in situ from the carboxylic acid and the base corresponding to the "onium" cation. If the acid is unstable, such as a beta-ketocarboxylic acid with a tendency to decompose, a different carboxylic acid can be used initially. For example, instead of 4,4,4-trifluoroaceto-acetic acid, the trifluoroacetic acid can initially be used in order to obtain the "onium" salt. Upon addition of 4,4,4-trifluoroacetoacetic acid or of an ester, the "onium" salt of the 4,4,4-trifluoroacetoacetic acid is formed by means of a gentle conversion without any decarboxylation.

The addition of an acid, such as a carboxylic acid, is not necessary and, preferably, such an acid is not added.

DETAILED DESCRIPTION OF PREFERRED EMBODIMENTS

In principle, the inventive method can be used for the synthesis and purification of any carboxylic acids, acid chlorides and esters of any carboxylic acids with any alcohols. In accordance with a preferred embodiment, a carboxylic acid having the formula $R^1C(O)OH$ or $R^1C(O)CH_2C(O)OH$, a carboxylic acid chloride of the formula $R^1C(O)Cl$ (I) or $R^1C(O)CH_2C(O)Cl$ (II), an ester of the formula $R^1C(O)OR^2$ (III) or of the formula $R^1C(O)CH_2C(O)OR^2$ (IV) is used, wherein $R^1$ represents an alkyl group with 1 to 6 carbon atoms and substituted by at least one halogen atom, especially by at least 1 fluorine atom, and $R^2$ represents alkyl or alkenyl with 1 to 8 carbon atoms, alkyl substituted by at least 1 halogen atom or alkenyl with 1 (or in the case of alkenyl with at least 2 carbon atoms) to 8 carbon atoms, phenyl, tolyl, benzyl or phenyl, tolyl, benzyl substituted by at least 1 halogen atom and/or at least one nitro group. The method is particularly suitable for use with compounds of formula $R^1C(O)OH$ of formula (I), of formula (II) (the compounds of formula (II) being obtainable, for example, by the addition reaction between compounds of formula (I) and ketene) and of formulas (III) or (IV), in which $R^1$ represents polyfluorinated, perfluorinated or polyfluorochlorinated alkyl with 1 to 6 carbon atoms and, in particular, 1 to 4 carbon atoms. In this connection, "polyfluorinated" means that at least ⅔ of all hydrogen atoms in $R^1$ are exchanged for fluorine atoms. "Perfluorinated" means that all hydrogen atoms in $R^1$ are exchanged for fluorine atoms. "Polyfluorochlorinated" means at least ⅔ of all hydrogen atoms are exchanged for fluorine atoms and, of the remaining hydrogen atoms, at least the majority or all are exchanged for chlorine atoms.

Furthermore, the use of an ester or alcohol having the formula $R^2OH$ (II) is preferred. In $R^2OH$, $R^2$ represents alkyl or alkenyl with 1 to 8 carbon atoms, alkyl substituted by at least 1 halogen atom or alkenyl with 1 (or in the case of alkenyl with at least 2 carbon atoms) to 8 carbon atoms, phenyl, tolyl, benzyl or phenyl, tolyl, benzyl substituted by at least 1 halogen atom and/or at least one nitro group.

It is especially preferred when $R^1$ represents polyfluoroalkyl, perfluoroalkyl or polychlorofluoroalkyl with 1 to 4 carbon atoms and $R^2$ represents alkyl or alkenyl with 1 (or in the case of alkenyl with at least 2 carbon atoms) to 4 carbon atoms, alkyl or alkenyl with 1 (or in the case of alkenyl with at least 2 carbon atoms) to 4 carbon atoms by at least 1 halogen atom or phenyl, substituted by at least 1 halogen atom and/or at least by one nitro group. In particular, $R^1$ represents perfluoromethyl, perfluoroethyl, perfluoropropyl or chlorodifluoromethyl. It is especially preferred when $R^2$ represents alkyl or alkenyl with 1 (or in the case of alkenyl with at least 2 carbon atoms) to 3 carbon atoms, alkyl or alkenyl with 1 (or in the case of alkenyl with at least 2 carbon atoms) to 3 carbon atoms substituted by at least 1 fluorine atom, phenyl or phenyl substituted by at least 1 fluorine atom and/or at least one nitro group.

Carboxylic acid chlorides, substituted by fluorine and optionally by chlorine, can be synthesized by known methods.

"Onium" is a cation with a positively charged nitrogen, such as protonated, aromatic nitrogen bases like pyridinium or protonated alkyl-, dialkyl- or trialkylammonium cations with up to 20 carbon atoms or ammonium compounds substituted by cycloalkyl or cycloaliphatic nitrogen bases, such as pyridinium or quaternary ammonium cations.

Very suitable as carboxylic acid salts are "onium" salts, in which "onium" represents a cation of nitrogen having the formula $R^IR^{II}R^{III}R^{IV}N^+$, wherein $R^I$, $R^{II}$, $R^{III}$ and $R^{IV}$ independently of one another are hydrogen, alkyl with 1 to 20 carbon atoms, aryl or alkaryl or wherein $R^I$ and $R^{II}$ or wherein $R^{III}$ and $R^{IV}$ or wherein $R^I$, $R^{II}$ and $R^{III}$ or wherein $R^I$, $R^{II}$, $R^{III}$ and $R^{IV}$, optionally with inclusion of the nitrogen atom, form saturated or unsaturated ring systems. "Aryl", in particular, here refers to phenyl or to phenyl substituted by one or more $C_1$- to $C_2$ alkyl groups. Outstandingly suitable are salts, in which "onium" represents ammonium, pyridinium or $R^{1'}R^{2'}R^{3'}R^{4'}N^+$, wherein $R^{1'}$, $R^{2'}$, $R^{3'}$ and $R^{4'}$ independently of one another represent hydrogen, alkyl with 1 to 15 carbon atoms, phenyl or benzyl. Pyridinium, piperidinium, anilinium, benzyltriethylamrnonium and triethylammonium are named as examples of such cations.

The inventive method is particularly suitable for the production and purification of difluoroacetic acid, 4,4-difluoroacetoacetic acid, trifluoroacetic acid, chlorodifluoroacetic acid, 4,4,4-trifluoroacetoacetic acid and 4-chloro-4,4-difluoroacetoacetic acid, their acid chlorides and the esters with 1,1,1-trifluoroethanol, methanol, ethanol, isopropanol, n-propanol, 4-nitrophenol, pentafluorophenol and allyl alcohol.

For the ester synthesis, the molar ratio of carboxylic acid halide to alcohol advantageously is greater than 0.9. The alcohol can also be used in a larger excess and serves as solvent, particularly if the alcohol is substituted by electron withdrawing groups, such fluorine atoms or a substituted alcohol. Advisably, the molar ratio of alcohol to carboxylic acid halide is between 0.9:1 and 1.1:1 or, in the event that the alcohol acts as solvent, up to 5:1.

The temperature, at which the reaction (or the purification) is carried out ranges, from room temperature (about 20° C.) up to the boiling point of the mixture, for example, up to 100°C. If the acids or acid chlorides are unstable, the reaction is carried out below the decarboxylation temperature. This is the case, for example, for the esterification of 4,4,4-trifluoro-, 4-chloro-4,4-difluoro- and 4,4-difluoroacetoacetic acid chloride; the reaction is carried out here at room temperature or with cooling and at ambient pressure (about 1 bar abs.) or, if so desired, at an elevated pressure, such as a pressure or up to 5 bar absolute.

The "onium" salt may be present in catalytic or molar amounts. Advisably, the molar ratio of acid chloride to carboxylic acid salt ranges from 1:1 up to 20,000:1.

Aside from the already mentioned distillation, the fact that two phases are formed in the case of some esters can also be used for the isolation of the esters. One phase then contains the very pure ester (in a purity greater than 94%) and the other phase contains the catalyst, the alcohol and the fluoride. Two phases are formed, for example, in the case of methyl and ethyl esters of trifluoro- and chlorodifluoroacetic acid, as well as in the case of the n-propyl ester of chlorodifluoroacetic acid. This has the advantage that the working up is simplified.

For this embodiment of the inventive method of synthesizing methyl or ethyl esters of trifluoroacetic acid and of chlorodifluoroacetic acid and the n-propyl ester of chlorodifluoroacetic acid, the acid chloride is reacted with an excess of the alcohol in the presence of an "onium" salt of the acid in question and the molar ratio of alcohol to acid chloride is selected so that two phases are formed, one phase containing the ester in a purity of at least 95%, which can be achieved without distillation and the ester being isolated by separating the ester phase from the other phase. With this procedure, an ester is obtained in a purity, which makes distillation superfluous. In a preferred embodiment of the inventive method, the ester obtained is therefore isolated without distillation.

For the synthesis of the methyl ester of trifluoroacetic acid, the molar ratio of methanol to trifluoroacetyl chloride ranges from 1.03:1 to 4:1. For the synthesis of the ethyl ester of trifluoroacetic acid, the molar ratio of ethanol to trifluoroacetyl chloride ranges from 1.01:1 to 5:1. For the synthesis of the methyl ester of chlorodifluoroacetic acid, the molar ratio of methanol to chlorodifluoroacetyl chloride ranges from 1.06:1 to 2.5:1. For the synthesis of the ethyl ester of chlorodifluoroacetic acid, the molar ratio of ethanol to chlorodifluoroacetyl chloride ranges from 1.02:1 to 2.5:1. In the ranges named, there are two phases, one of which comprises the ester, which is always contained in a purity of at least 95% by weight. The methyl esters always form the lower phase; the ethyl ester of chlorodifluoroacetic acid also forms the lower phase, whereas the ethyl ester of trifluoroacetic acid forms the upper phase.

The invention yields acids, acid chlorides and esters with a greatly reduced fluoride content (for example, of less than 70 ppm, and even of 10 ppm and less), depending on the amount of hydrogen fluoride, carboxylic acid fluoride and hydrolyzable fluoride originally contained. On the one hand, the product accordingly is very pure. On the other, there are no corrosion problems (or greatly reduced corrosion), for example, during the esterification in plants and plant components of ceramic or glass.

The use of "onium" salts as catalysts for the esterification was disclosed already in the EPA 623 582 (=U.S. Pat. No. 5,405,991). It is not evident from this application that the synthesis is possible very easily in this manner and that, when carboxylic acid fluoride-containing starting materials are used, a low-fluoride product is obtained and the corrosion is reduced. The same is true for the unpublished DE 197 32 031, which relates to the two-phase method of synthesizing methyl and ethyl esters of $CF_3C(O)Cl$ and $CF_2ClC(O)Cl$.

"Onium" salts of 4,4,4-trifluoroacetoacetic acid, of 4-chloro-4,4-difluoroacetoacetic acid and of 4,4-difluoroacetoacetic acid as well as the free acids are novel, can be used for the inventive method and are also an object of the invention.

The invention is described in greater detail by means of the following examples, without being limited in its scope.

General Method for Examples 1 to 3 for the Synthesis of Low-Fluoride Ethyl Trifluoroacetates from Trifluoroacetyl Chloride and Ethanol using a Catalyst Formulation (for Examples 1 to 3):

| | | |
|---|---|---|
| 0.2 moles | pyridine | 15.8 g |
| 0.2 moles | trifluoroacetic acid (TFA) | 22.8 g |
| 2.0 moles | ethanol, analytical grade | 92.1 g |
| 1.8 moles | trifluoroacetyl chloride (TFAC) | 238.5 g |

Method:

Pyridine is added to a 250 ml, 3-neck flask with magnetic stirrer, thermocouple and dry ice cooler and TFA is added dropwise. The reaction is exothermic and, before the salt was able to precipitate completely, ethanol was added in order to keep the salt in solution. To speed up the reaction, the solution was heated in an oil bath to 50° C. and, at this temperature, the TFAC is introduced through a sintered glass disk. When 20% of the TFAC required has been added, two phases are formed, the upper phase being almost pure ethyl trifluoroacetate.

When all of the TFAC had been introduced, stirring was continued for a further 30 minutes, after which the products were transferred to a separating funnel. When separated, the two phases are clear, the catalyst phase being colored a light yellow.

EXAMPLE 1

TFAC with a fluoride content of 570 ppm was used. The experimental procedure was as described above and, after the reaction, yielded an ester phase with a fluoride content of 61 ppm and a catalyst phase with 1850 ppm of $F^-$.

The percentage distribution showed that the fluoride preferentially was in the catalyst phase, where 86.03% was found; the ester phase contained 15.27%.

EXAMPLE 2

The same fluoride with a fluoride content of 570 ppm was used here. The experimental procedure was as described above, however, with distinctly more vigorous stirring. After the reaction, an ester phase with 10 ppm and a catalyst phase with 3,670 ppm of $F^-$ were obtained.

The percentage distribution showed that fluoride is present preferentially in the catalyst phase, where 92.28% were found. In the ester phase, the fluoride was reduced to 2.72% of the original value.

EXAMPLE 3

TFAC with a fluoride content of 71 ppm was used here. The experimental procedure was as described above and, after the reaction, an ester phase with a fluoride content of 10 ppm and a catalyst phase with a fluoride content of 130 ppm were obtained.

The percentage distribution showed that fluoride is present preferentially in the catalyst phase, where 76.66% of the total fluoride were found. In the ester phase, the fluoride was reduced to 23.35% of the original value.

The examples show that the fluoride value in the ester can be reduced to very small values when the fluoride content in the acid fluoride originally is very high, as well as when it is already very low.

EXAMPLE 4

Formulation:

| | |
|---|---|
| 0.1 moles of pyridine | 7.9 g |
| 0.1 moles of trifluoroacetic acid | 11.4 g |
| 2.0 moles of analytical grade ethanol | 92.1 g |
| 1.8 moles of trifluoroacetyl chloride | 238.5 g |

TFAC with a fluoride content of 570 ppm was used here. The amount of catalyst was reduced to 5 mole percent instead of the 10 mole used otherwise. The experimental procedure was as described above, with the exception that stirring was more vigorous. After the reaction, an ester phase with a fluoride content of 32 ppm was obtained.

EXAMPLE 5

Preparation of Low-Fluoride Trifluoroacetate Ester Using $SiO_2$ in a Stirred Ceramic Vessel 5.1 A solution of 0.10 kg of pyridinium trifluoroacetate in 1.90 kg of methanol was prepared and mixed with a further 4.80 kg of methanol and 0.02 kg of precipitated silica hydrate (Product "1.00656.000 silica, precipitated, highest purity, heavy" of Merck KGaA, Darmstadt, with a bulk density of about 30 to 50 g/100 mL and a particle size of less than 0.1 mm) was added and 19.2 kg of trifluoroacetyl chloride (1,000 ppm hydrolyzable fluoride) were passed in with stirring. After the distillation, the methyl ester contained less than 40 ppm of hydrolyzable fluoride. Even after many repetitions, corrosion could not be detected at the ceramic parts of the stirred vessel.

5.2 Example 5.1 was repeated. Instead of methanol, the same molar amount of ethanol was used. After the distillation, the ethyl ester contained less than 30 ppm of hydrolyzable fluoride.

EXAMPLE 6

Separating Hydrolyzable Fluoride from Trifluoroacetyl Chloride

A glass tube with an internal diameter of 1.5 cm was filled with 100 g of KC Trockenperlen AF 125 produced by Englehard Process Chemicals GmbH, Hannover. These dry beads consist of silica gel and have a diameter between 2 and 5 mm. The pore diameter is 125 Å (12.5 mm). They are usually used as a drying agent or as a catalyst support.

Trifluoroacetyl chloride with 570 ppm of hydrolyzable fluoride is passed at room temperature over this filling. The product leaving the filling contains 98 ppm.

EXAMPLES 7–9

Purification of Ethyl 4,4,4-Trifluoroacetate

The ester (630 g, 3.4 moles) was mixed with 2.6 g of hydrogen fluoride (0.1 mole) in order to simulate an ester contaminated with 4125 ppm of hydrolyzable fluoride.

EXAMPLE 7

Pyridine-TFA as Agent for Separating Fluoride

Pyridine (2.1 g, 0.027 moles) was added to a 250 ml Teflon flask with magnetic stirrer and combined with 3.1 g of trifluoroacetic acid (0.027 moles) (4,4,4-trifluoroacetoacetic acid tends to decarboxylate during the direct synthesis of the salt of pyridine and 4,4,4-trifluoroacetoacetic acid). To the pyridinium trifluoroacetate, 50.2 g of ethyl 4,4,4-trifluoroacetoacetate was added and stirred at room temperature for 3 hours. After this time, the solution was heated for 1 hour at a water bath temperature of 70° C. and distilled under vacuum. The residue, in which the "onium" salt of 4,4,4-trifluoroacetoacetic acid was detected ($^{19}$F-NMR) had a fluoride content of 14,500 ppm. The ester, which was distilled off, still contained 1460 ppm of fluoride.

Similarly, it was also possible to produce the "onium" salts of 4,4-difluoroacetoacetic acid and of 4-chloro-4,4-difluoroacetoacetic acid, which can be isolated by standard methods.

EXAMPLE 8

Precipitated Silica Hydrate as Absorbent

The ethyl 4,4,4-trifluoroacetoacetate (50.1 g, 0.27 moles) was added here to a Teflon flask having a magnetic stirrer. Precipitated silica hydrate (6.57 g) of Merck (see Example 5) was added to the ethyl 4,4,4-trifluoroacetoacetate and stirred for 3 hours at room temperature. At the end of this time, the solution is heated for 1 hour at a water bath temperature of 80° C. At the end of the stirring time, the solution is filtered off hot and analyzed for fluoride. A fluoride content of 9 ppm was obtained.

EXAMPLE 9

Silica Gel Beads as Absorbent

The ethyl 4,4,4-trifluoroacetoacetate (50.7 g, 0.28 moles) was added here to a Teflon flask having a magnetic stirrer. 10.2 g of "AF 125" drying beads (for further details, see Example 6) were added to the ethyl 4,4,4-trifluoroacetoacetate and stirred for 3 hours at room temperature. At the end of this time, the ethyl 4,4,4-trifluoroacetoacetate was filtered off, fluoride content: 47 ppm.

EXAMPLE 10

Purification of Trifluoroacetic Acid

Trifluoroacetyl chloride containing about 1000 ppm of hydrolyzable fluoride was stirred with an almost equimolar amount of water. The reaction mixture was passed continuously in a circuit over "AF 125". Less than 50 ppm of hydrolyzable fluoride were detected in the product. Thus the silica absorbs the fluoride in spite of the water content of the reaction mixture.

EXAMPLE 11

Preparation and Isolation of 4,4,4-Trifluoroacetoacetic Acid

Formulation:

| 4.0 moles | ethyl, α,α,α-trifluoroacetoacetate | 736.4 g |
| 2.0 moles | trifluoroacetic acid | 228.0 g |
| 0.9 moles | sulfuric acid (95–97%) | 90.0 g |

Synthesis and Implementation:

Ethyl α,α,α-trifluoroacetoacetate and trifluoroacetic acid were added to a 1 liter flask with distillation head, and concentrated sulfuric acid was carefully added dropwise. The initially clear solution became cloudy. After that, the solution was heated for about 1.5 hours at 70° to 90° C. When isolated gas bubbles were observed to occur at the bubble counter, the temperature was lowered somewhat.

After the heating, the light brown solution was taken out of the oil bath and placed in an ice bath for cooling, fine white needle-shaped crystals forming after a short time. The crystals were filtered out over a sintered glass plate, analyzed by means of NMR and mass spectrometry and confirmed to be trifluoroacetoacetic acid.

In an analogous manner, 4,4-difluoroacetoacetic acid and 4-chloro-4,4,-difluoroacetoacetic acid can be obtained from the ethyl ester and trifluoroacetic acid and subsequent conventional purification.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method for producing a fluorinated organic compound with a decreased content of hydrolyzable fluoride, said method consisting essentially of the step of contacting a fluorinated organic compound contaminated with hydrolyzable fluoride with at least one inorganic oxide sorption agent.

2. The method according to claim 1, wherein said contaminated fluorinated organic compound is a carboxylic acid or a carboxylic acid chloride.

3. The method according to claim 1, wherein said contaminated fluorinated organic compound is a product of a condensation reaction of a carboxylic acid or of a carboxylic acid chloride.

4. The method according to claim 3, wherein said product of a carboxylic acid or carboxylic acid chloride is subjected to said contacting step as part of a process of synthesizing said product.

5. The method according to claim 1, wherein said inorganic oxide sorption agent is an inorganic oxide absorbent.

6. The method according to claim 5, wherein said inorganic oxide absorbent comprises $SiO_2$.

7. The method according to claim 5, wherein said inorganic oxide absorbent comprises silica gel beads or precipitated silica hydrate.

8. The method for synthesizing a compound selected from the group consisting of fluorinated carboxylic acids, carboxylic acid chlorides and carboxylate esters with a decreased carboxylic acid fluoride or a decreased hydrolyzable fluoride content, comprising contacting a fluorinated carboxylic acid, carboxylic acid chloride or carboxylate ester which is contaminated with carboxylic acid fluoride or with hydrolyzable fluoride, with at least one separating agent for carboxylic acid fluoride and hydrolyzable fluoride comprising an inorganic oxide absorbent to obtain said fluorinated carboxylic acid, carboxylic acid chloride or carboxylate ester with a decreased carboxylic acid fluoride or a decreased hydrolyzable fluoride content.

9. The method according to claim 8, wherein said carboxylate ester is synthesized from a carboxylic acid chloride and an alcohol, and wherein the carboxylic acid chloride and alcohol are reacted in the presence of an inorganic oxide absorbent.

10. The method according to claim 1, wherein said organic compound is selected from the group consisting of carboxylic acids corresponding to the formula $R^1C(O)OH$, and carboxylic acid chlorides corresponding to the formula $R^1C(O)Cl$ (I) or the formula $R^1C(O)CH_2C(O)Cl$ (II); wherein $R^1$ represents an alkyl group with 1 to 6 carbon atoms, substituted by at least 1 halogen atom.

11. The method according to claim 10, wherein $R^1$ represents a polyfluoroalkyl, perfluoroalkyl or polyfluorochloroalkyl group with 1 to 6 carbon atoms.

12. The method according to claim 9, wherein said alcohol corresponds to the formula $R^2OH$ (V), in which $R^2$ represents an alkyl or alkenyl group with 1 to 8 carbon atoms, an alkyl or alkenyl group with 1 to 8 carbon atoms substituted by at least one halogen atom, a phenyl, tolyl or benzyl group, or a phenyl, tolyl or benzyl group substituted by at least one halogen atom or at least one nitro group.

13. The method according to claim 9, wherein an ester corresponding to the formula $R^1C(O)OR^2$ (III) or to the formula $R^1C(O)CH_2C(O)OR^2$ (IV) is purified or synthesized; $R^1$ represents an alkyl group with 1 to 6 carbon atoms, substituted by at least 1 halogen atom, and $R^2$ represents an alkyl or alkenyl group with 1 to 8 carbon atoms, an alkyl or alkenyl group with 1 to 8 carbon atoms substituted by at least one halogen atom, a phenyl, tolyl or benzyl group, or a phenyl, tolyl or benzyl group substituted by at least one halogen atom or at least one nitro group.

14. The method according to claim 13, wherein $R^1$ represents a polyfluoroalkyl, perfluoroalkyl or polyfluorochloroalkyl group with 1 to 4 carbon atoms, and $R^2$ represents an alkyl or alkenyl group with 1 to 4 carbon atoms, an alkyl or alkenyl group with 1 to 4 carbon atoms substituted by at least one halogen atom, a phenyl group, or a phenyl group substituted by at least one halogen atom or at least one nitro group.

15. The method according to claim 14, wherein $R^1$ represents a perfluoromethyl group, a perfluoroethyl group, a perfluoropropyl group or a chlorodifluoromethyl group.

16. The method according to claim 15, wherein $R^2$ represents an alkyl or alkenyl group with 1 to 3 carbon atoms, an alkyl or alkenyl group with has 1 to 3 carbon atoms which is substituted by at least one fluorine atom, a phenyl group, or a phenyl group substituted by at least one fluorine atom or at least one nitro group.

17. The method according to claim 10, wherein said organic compound is a carboxylic acid chloride corresponding to the formula $R^1C(O)CH_2C(O)Cl$, which was obtained by reacting an acid chlroide corresponding to the formula $R^1C(O)Cl$ and ketene.

18. The method according to claim 1, wherein said fluorinated organic compound contaminated with hydrolyzable fluoride is $CF_3C(O)Cl$ or $CF_3C(O)CH_2C(O)Cl$.

19. The method according to claim 7, wherein silica gel beads are used in a aqueous system and purification is effected in a bypass stream.

20. 4-chloro-4,4-difluoroacetoacetic acid, 4,4-difluoroacetoacetic acid or an "onium" salt thereof.

* * * * *